United States Patent [19]

Granik et al.

[11] Patent Number: 4,839,380

[45] Date of Patent: Jun. 13, 1989

[54] 1-THIOCARBAMOYLMETHYLPYRROLI-DINE-2-THIONE, MEDICAL COMPOSITIONS OF, AND ANTI-HYPOXIC AND NOOTROPIC USE THEREOF

[76] Inventors: Vladimir G. Granik, Kona-kovsky proezd, 19, kv. 64, Moscow; Tatyana V. Stezhko, ulitsa Severnaya, 8, kv. 30, Moskovskaya oblast, Odintsovo; Robert G. Glushkov, ulitsa Gorkogo, 43, kv. 90, Moscow; Mikhail D. Mashkovsky, Lenin-gradsky prospekt, 75a, kv. 55, Moscow; Lidia F. Roschina, Rostov-skaya naberezhnaya, 3, kv. 135, Moscow; Antonina I. Polezhaeva, ulitsa 13 Parkovaya, 25, korpus I, kv. 6, Moscow; Roza B. Parimbetova, ulitsa I. Babushkina, 3, kv. 217, Moscow; Jury G. Bobkov, ulitsa Latsisa, 33, korpus I, kv. 7, Moscow; Alexandr S. Losev, ulitsa Bekhtereva, 7, korpus I, kv. 42, Moscow; Irina A. Ivanova, Volóko-lamskoe shosse, 14, kv. 41, Moscow, all of U.S.S.R.

[21] Appl. No.: 198,999

[22] PCT Filed: Aug. 25, 1986

[86] PCT No.: PCT/SU86/00080

§ 371 Date: Apr. 4, 1988

§ 102(e) Date: Apr. 4, 1988

[87] PCT Pub. No.: WO88/01620

PCT Pub. Date: Mar. 10, 1988

[51] Int. Cl.$^4$ .................. C07D 207/24; A61K 31/40
[52] U.S. Cl. ............................. 517/424; 548/550
[58] Field of Search ................ 514/424; 548/550

[56] References Cited

FOREIGN PATENT DOCUMENTS

88/01620  3/1988  U.S.S.R. .

*Primary Examiner*—David B. Springer
*Attorney, Agent, or Firm*—Burgess, Ryan & Wayne

[57] ABSTRACT

A novel compound, namely, 1-thiocarbamylmethylpyrrolidine-2-thione has the following formula:

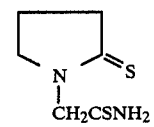

A process for preparing said compound comprises reacting a derivative of pyrrolidone-2 of the general formula:

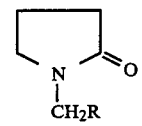

wherein R is nitrile or carbamoyl, with phosphorus pentasulphide in an inert non-polar solvent at a temperature above room temperature, followed by treatment of the resulting precipitate with water upon boiling and isolation of the desired product.

The compound according to the present invention exhibits antihypoxic and nootropic activity.

4 Claims, No Drawings

1-THIOCARBAMOYLMETHYLPYRROLIDINE-2-THIONE, MEDICAL COMPOSITIONS OF, AND ANTI-HYPOXIC AND NOOTROPIC USE THEREOF

FIELD OF THE ART

The present invention relates to organic chemistry and, more particularly, to a novel compound, viz., 1-thiocarbamylmethylpyrrolidine-2-thione, and to a process for preparing same. Said compound exhibits antihypoxic and nootropic activity.

PRIOR ART

Known in the art are different compounds exhibiting antihypoxic and nootropic activity, for instance, 1-carbamidomethylpyrrolidone-2 of the formula

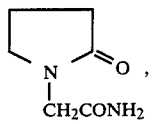

which is an active principle of the pharamcological preparation pyracetam (cf. Mashkovsky M. D., Roshcina L. F., Polezhaeva A. I., "Some Specific Features of Pharmacological Action of Pyracetam", Farmakologia i Toksikologia, No. 6, 1977, pp. 676–684).

Pyracetam is the main representative of a novel class of pharmacologically active compounds-nootropics, whose main pharmacological characteristics reside in producing a protective effect in various forms of oyxgen deficiency (antihypoxic effect) and a positive effect on the processes of learning and memory.

Pyracetam exhibits nootropic activity only when used in high doses: from 500 to 2000 mg/kg.

Furthermore, pyracetam is characterized by the absence of a pronounced stimulative effect on the mechanisms of memory consolidation and performance of conditioned reflexes.

DISCLOSURE OF THE INVENTION

The compound of the present invention is novel and has not been described in the literature.

The present invention is directed to the provision of a novel compound possessing simultaneously an increased antihypoxic and nootropic activity and a low toxicity.

This object is accomplished due to the fact that the novel compound, 1-thiocarbamylmethylpyrrolidine-2-thione, according to the invention, has the following formula:

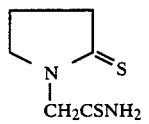

The compound of the invention is a crystalline substance, soluble in N,N-dimethylformamide, crystallizing from water, alcohols, ethylacetate, chloroform, benzene, acetaone, insoluble in ether, hexane, stable in storage, m.p. 156°–158° C. (from isopropanol).

The structure of the compound has been identified by the data of elemental analysis; IR spectrum displaying bands at 1630, 3110, and 3260 $cm^{-1}$ ($NH_2$-group) and 1120 $cm^{-1}$ (C=S); mass spectrum comprising a peak of molecular ion 174 m/z, and according to which the compound comprises two atoms of sulphur.

Best Way of Carrying the Invention into Effect

The compound according to the present invention has been tested for antihypoxic and nootropic activity in experiments on animals.

The antihypoxic effect of the compound according to the present invention was studied in comparison with pyracetam on various experimental models of hypoxic states in experiments on mice and rats. The compound according to the present invention and pyracetam were administered intraperitoneally in the form of an aqueous emulsion prepared with Tween-80.

Tests were carried out on a model of an acute hypoxic hypoxia with hypercapnia.

The tests were conducted using 540 nondescript while male mice with a mass of 20–22 g. Each mouse was separately placed into a sealed chamber (with the capacity of 250 ml) 60 minutes after administration of the compound according to the present invention in the doses of 50, 100, 250, 500 and 750 mg/kg. The control animals were issued with an isotonic solution of sodium chloride. The antihypoxic activity was assessed by the lifespan of the mice in the sealed chamber (in minutes).

The results of the study of antihypoxic effect of the compound according to the present invention in comparison with the prior art preparation—pyracetam—are given in Table 1 hereinbelow.

As it is seen from the experimental data given in Table 1, the compound according to the present invention extended, as compared to the control, the mice lifespan under conditions of an acute hypoxic hypoxia by about 2 times already at the dose of 100 mg/kg, whereas at the dose of 750 kmg/kg—by 4 times (324.5% increase) which demonstrates its high antihypoxic activity. In its antihypoxic effect the compound according to the present invention is considerably superior to pyracetam. Thus, the compound of this invention in the dose of 100 mg/kg extends the lifespan of the mice up to 56.3 minutes (by 10.39%) as compared to the control (28.1 minutes), whereas pyracetam in the dose exceeding by 20 times that of the compound according to the present invention, i.e. in the dose of 2,000 mg/kg extends it only to 45 minutes (or by 60% as compared to the control).

Therefore, on a model of an acute hypoxic hypoxia with hypercapnia it has been found that the compound according to the present invention beginning with the dose of 100 mg/kg is capable of enhancing the animal organism's resistance to an acute oxygen insufficiency and extends the lifespan of mice under hypoxia conditions.

The studies were carried out on a model of an acute hypobaric hypoxia.

An acute hyperbaric hypoxia was modelled in a flow-type barometric chamber at an ambient temperature of 17°–20° C. with absorption of carbon dioxide and water.

TABLE 1

Effect of test compounds on the lifespan of mice (in minutes) under conditions of acute hypoxic hypoxia

| Nos | Compounds | Doses, mg/kg | | | | | | |
|---|---|---|---|---|---|---|---|---|
| | | 0 | 100 | 250 | 500 | 750 | 100 | 2000 |
| 1 | 2 | 3 | 4 | 5 | 6 | 7 | 8 | 9 |
| 1 | Control | 28.1 (22.5–33.7) | — | — | — | — | — | — |
| 2 | Compound of the present invention | — | 56.3 (43.7–68.9) | 60.3 (50.0–70.6) | 95.2 (87.1–103.3) | 119.2 (115.7–122.7) | not studied | not studied |
| 3 | Pyracetam | — | 27.4 (21.4–33.4) | 33.5 (29.1–37.9) | 39.6 (35.5–43.7) | 34.4 (29.8–38.0) | 41.4 (40.2–42.6) | 45.0 (39.1–50.9) |

The test animals (male mice, tetrahybrids) with a mass of 15–22 g of the same generation were "lifted" (under simulation conditions) at the mean speed of 50 m/sec to the height of 11,000 m at which the lifespan (in minutes) for the same series of experiments was evaluated. Furthermore, the mice were discretely lifted at the same speed to the height of 10,000 m where they stayed for 1 minute and then to the height of 11,000 m, where they again were kept for 1 minute and so on, till their death for the determination of the height "ceiling", The animals' death was adjudicated by the occurrence of an agonal breathing against the background of convulsions. The total number of mice employed in the experiments was 200.

As the comparison preparation pracetam was used. The compound according to the present invention and pyracetam were administered one hour before the "lift". The results of the experiments were statistically evaluated using T-criterion and Student's modification followed by comparison with the control data assumed as 100%.

Similar experiments were conducted with nondescript male rate with a mass of 180–230 g in the same barometric chambers with ascending to the height of 12,000 m.

The results of the experiments on the model of an acute hypobaric are shown in Tables 2 and 3 hereinbelow.

Investigations were also carried out with a model of an acute normobaric hypoxia.

An acute normobaric hypoxia was simulated in a flow-type barometric chamber at an ambient temperature of 17°–22° C. with absorption of carbon dioxide and water. A gas mixture (7% of $N_2$ and 3% of $O_2$) was admitted into the barometric chamber at the rate of 10 l/min. The lifespan of test animals (mice, rats) in the chambers was recorded since the moment of the mixture admission into the chamber till the moment of perdition of the animals which was adjudicated by an agonal breathing against the background of convulsions. The modes of administration of the preparations, species of animals and analysis of the results of the experiments are similar to those described hereinbefore for the case of an acute hypobaric hypoxia. The experiments were carried out using 50 mice and 20 rats.

The test results are shown in the following Table 4.

The experimental data thus obtained demonstrate that the compound according to the present invention in the dose of 250 mg/kg increase resistance of mice to an acute normobaric hypoxia by 4.5 times (differences are certain) that of rats—by 1.5 times as compared to the control and is superior to pyracetam in its effectiveness for this type of hypoxia for the dose of 250 mg/kg by 5 times, for the dose of 500 mg/kg—by 3.2 times on mice and by 1.5 times on rats.

TABLE 2

Effect of the compound according to the present invention on lifespan of mice (in minutes) at the height of 11,000 m

| Compound | Doses, mg/kg | | | |
|---|---|---|---|---|
| | 0 Control | 100 | 250 | 500 |
| Pyracetam | 6.1 ± 2.75 100.0 ± 45.1% | inactive | 6.16 ± 0.72 101.0 ± 11.8% P > 0.5 | 8.13 ± 2.43 133.3 ± 39.9% P > 0.5 |
| Compound of the present invention | 6.1 ± 2.75 100.0 ± 45.1% | 12.58 ± 8.64 206.2 ± 59.7% 0.1 < P < 0.2 | 19.97 ± 4.93 327.4 ± 80.8% P < 0.05 | 30.0 ± 0 491.8 ± 0.0% P < 0.001 | low.

The experimental data show taht the compound according to the present is considerably superior to pyracetam in its antihypoxic activity on this model both in the effect on the lifespan duration at the "height" of 11,000m (by 3–4 times more effective) and in increase of the height ceiling (the compound according to the present invention elevates the height ceiling by 4,000 m as compared to the control and pyracetam in the dose of 500mg/kg).

TABLE 3

Effect of the compound according to the present invention on the height ceiling for mice ($H_{max}$, thous. m)

| Compound | Doses, mg/kg | | |
|---|---|---|---|
| | 0 Control | 250 | 500 |
| Pyracetam | 11.21 ± 0.441 | 10.96 ± 0.91 (P > 0.5) | 11.55 ± 0.62 (P > 0.5) |
| Compound of the present invention | 11.21 ± 0.441 | 14.0 ± 0.707 (P < 0.005) | 15.57 ± 0.85 (P < 0.001) |

TABLE 4

Effect of the compound according to the present invention on lifespan of experimental animals (in minutes) at an acute normobaric hypoxia

| Animals | Compounds | Doses, mg/kg | | |
|---|---|---|---|---|
| | | 0 Control | 250 | 500 |
| Mice | Pyracetam | 4.25 ± 0.54 | 3.73 ± 0.254 | 6.08 ± 0.744 |
| | | 100.0 ± 12.6% | 87.7 ± 5.97% | 143.1 ± 17.5% |
| | | | ($P > 0.5$) | ($0.05 < P < 0.1$) |
| | Compound of the present invention | 4.73 ± 0.367 | 22.21 ± 3.23 | —* |
| | | 100.0 ± 7.75% | 469.5 ± 68.3% | |
| | | | ($P < 0.001$) | |
| Rats | Pyracetam | 18.6 ± 3.61 | — | 17.3 ± 5.25 |
| | | 100.0 ± 19.4% | inactive | 93.0 ± 28.2% |
| | Compound of the present invention | 18.6 ± 3.61 | 27.38 ± 7.07 | —* |
| | | 100.0 ± 19.4% | 147.2 ± 38.0% | |
| | | | ($0.1 < P < 0.2$) | |

*Note: Not advisable, since the effect is obtained at lower doses.

The studies were carried out using a model of an acute histotoxic hypoxia.

An acute histotoxic hypoxia was induced by way of a subcutaneous injection of sodium nitroprusside in the dose of 20 mg/kg. This mode of administration results in a 100% death of mice in 15-25 minutes after administration of the preparation. The lifespan of the mice was adjudicated after administration of sodium nitroprusside against the background of the test compounds (the compound according to the present invention and pyracetam) which was recorded by the arrest of breathing and heart. In this series of experiments 40 animals altogether were used.

The test results are shown in Table 5 hereinbelow. These data were obtained, as it has been already mentioned hereinbefore, using Student's T-criterion.

TABLE 5

Effect of test compounds on resistance of mice to an acute histotoxic hypoxia (lifespan in minutes)

| Compounds | Doses, mg/kg | | | |
|---|---|---|---|---|
| | 0 Control | 250 | 500 | 1.000 |
| Pyracetam | 19.5 ± 6.55 | — | 17.98 ± 1.49 | 20.97 ± 1.31 |
| | 100.0 ± 33.6% | inactive | 92.2 ± 7.62% | 107.6 ± 6.7% |
| | | | ($P > 0.5$) | ($P > 0.5$) |
| Compound of the present invention | 19.5 ± 6.55 | 24.2 ± 2.46 | 32.2 ± 4.95 | —* |
| | 100.0 ± 33.6% | 124.1 ± 12.6% | 165.5 ± 25.4% | |
| | | $p < 0.5$ | $0.1 < p < 0.2$ | |

Note: Not advisable, since the effect is attained at lower doses.

The results of this series of experiments demonstrate that the compound according to the present invention in the dose of 500 mg/kg is superior to pyracetam in the dose of 500 mg/kg and 1,000 mg/kg by 1.5 times in its effectiveness for this particular kind of a hypoxic effect.

The studies were conducted on a model of an acute repeating anoxia.

The studies were carried out in experiments on rats with a mass of 180-200 g with nichrome electrodes in the brain (cerebral) cortex; after tracheostomy the animals were connected to the artificial-breathing apparatus. Anoxia was induced by repeatedly switching-off the breathing for 90, 120, 150 and 180 seconds with 10-minutes' intervals therebetween. Electrocardiogram and electrocorticogram were recorded. 53 rats altogether were used in the experiments. The antihypoxic activity of the compound according to the present invention in comparison with pyracetam was assessed by the following parameters:

I—time till the disappearance of a cortex electrical activity after discontinuation of oxygen supply;

II—time till the appearance of an electrocorticogram after renewal of breathing;

III—total time of electrical "silence" of the cortex for each of the successive anoxiae.

The results of the experiments were statistically evaluated using Student's T-criterion.

The test results are shown in Tables 6 and 7 hereinbelow.

The results thus obtained demonstrate that the compound according to the present invention in the dose of 250 mg/kg has a clearly pronounced antihypoxic activity in the case of an asphyxial hypoxia; the time till disappearance of an electrocorticogram under the effect of the compound according to the present invention has extended by nearly 2 times, especially for the first and second anoxiae, while the time of recovery of the functional capacity of the brain has been considerably reduced.

TABLE 6

Effect of the compound according to the present invention in comparison with pyracetam on recorded parameters of electrical activity of the brain after a repeated hypoxia of different duration

| | | Duration of successive anoxiae in seconds | | | | | |
|---|---|---|---|---|---|---|---|
| | | 90 seconds | | | | | |
| | | Parameters (seconds) | | | | | |
| Nos | Compound | I | II | III | I | II | III |
| 1 | 2 | 3 | 4 | 5 | 6 | 7 | 8 |
| 1. | Control | 45.4 ± 3.8 | 22.4 ± 2.5 | 66.6 ± 6.0 | 48.6 ± 3.3 | 45.3 ± 3.5 | 110.5 ± 7.0 |
| 2. | Pyracetam | 76.7 ± 4.8 xxx | 5.3 ± 0.2 xxx | 17.8 ± 4.9 xxx | 85.8 ± 7.3 xxx | 21.8 ± 6.9 xx | 53.3 ± 12.0 xxx |

TABLE 6-continued

Effect of the compound according to the present invention in comparison with pyracetam on recorded parameters of electrical activity of the brain after a repeated hypoxia of different duration

| | | Duration of successive anoxiae in seconds | | | | | |
|---|---|---|---|---|---|---|---|
| | | | | | 90 seconds | | |
| | | Parameters (seconds) | | | | | |
| Nos | Compound | I | II | III | I | II | III |
| 3. | (1.000 mg/kg) Compound of the present invention (250 mg/kg) | 84.3 ± 1.3 xxx | 3.7 ± 1.5 xxx | 8.9 ± 3.5 xxx | 89.0 ± 6.2 xxx | 18.3 ± 2.6 xxx | 52.4 ± 5.6 xxx |
| 1 | 2 | 9 | 10 | 11 | 12 | 13 | 14 |
| 1. | Control | 60.1 ± 3.6 | 57.3 ± 12.6 | 147.9 ± 15.6 | 76.4 ± 6.9 | — | — |
| 2. | Pyracetam (1.000 mg/kg) | 95.0 ± 16.3 x | 67.6 ± 42.1 | 131.2 ± 53.8 | 79.4 ± 23.8 | — | — |
| 3. | Compound of the present invention (250 mg/kg) | 73.9 ± 7.5 | 64.6 ± 22.2 | 121.0 ± 25.0 | 94.4 ± 9.4 | 160.6 ± 83.8 | 216.9 ± 72.0 |

"x" - differences are certain with $P < 0.05$;
"xx" - $0.001 < P < 0.05$;
"xxx" - $P < 0.001$.
"—" - the parameter is not recorded, since the time of recovery of the electrocorticogram after admission of oxygen is equal to infinity (i.e. the cortex does not function).

TABLE 7

Effect of the compound according to the present invention in comparison with pyracetam on resistance of rats' cerebral cortex to asphyxial hypoxia

| Compound | Number of animals with retained electro-corticogram after the 1st anoxia *in % | Number of animals with recovered electro-corticogram after the 4th anoxia (in %) |
|---|---|---|
| 1 | 2 | 3 |
| Control | 8.3 | 15.0 |
| Pyracetam (1,000 mg/kg) | 12.5 | 14.3 |
| Compound of the present invention (250 mg/kg) | 44.0 | 100.0 |

The most clearly pronounced antihypoxic effect of the compound has been noted in the analysis of the number of animals with a recovered, after the 4-th anoxia, functional activity of the brain. While in the control and upon administration of pyracetam such animals were in the number of only 15%, in the case of administration of the compound according to the present invention in 100% of events recovery of an electrical activity of the brain was noticed which was 7 times more effective than in the case of pyracetam. At the same time, the compound according to the present invention caused an pronounced antihypoxic effect also in respect of the magnitude of retention of the electrocorticogram after the first 90-seconds' anoxia while being superior to pyracetam in activity by as much as 3 times in the dose of 1.000 mg/kg.

The experiments carried out for investigation into the antihypoxic activity of the compound according to the present invention have shown that the compound to this invention exhibits antihypoxic activity with various kinds of the hypoxic action (on all the models employed).

As regards its activity, the compound according to the present invention is superior to pyracetam in the extent of the antihypoxic effect in all cases of comparison and is more effective in considerably smaller doses as compared to pyracetam.

The compound according to the present invention was also tested for the effect produced thereby on processes of learning and memorizing.

The study of the compound according to the present invention for the speed of learning and performing the produced conditioned reflux was effected in experiments on rats using the method of electrodefensive conditioned reflexes of avoidance.

In experiments on mice the compound according to the present invention was tested for the effects produced thereby on processes of memory consolidation according to the results of investigation of the conditional response of passive avoidance.

The study of the effect on the learning speed and fulfilment of the elaborated conditioned reflex was effected on 40 nondescript male rats with a mass of 150170 g (4 groups of 10 rats in each) by the method of electrodefensive conditioned reflexes. Conditioned reflexes were trained in all rats for ringing used as a conditional irritation signal supported by a non-conditional irritating agent—electric current (40–50 V) supplied to an electrified floor of a conditioned-reflex chamber. As the criterion for the elaboration of the conditioned reflex the rat's jump onto a stand in response to switching-on of a bell during the first 10 seconds after the beginning of the sound was assumed.

All rats, against the background of elaboration of conditioned reflexes, were administered over 3 weeks (5 times a week) with: the first group—the compound according to the present invention in the dose of 250 mg/kg; the second and third group—pyracetam in the doses of 500 and 1,000 mg/kg; and the fourth group—control—isotonic solution of sodium chloride. The administration was effected intraperiotoneally 24 hours before the experiment.

It has been established that the compound according to the present invention in the dose of 250 mg/kg causes an accelerated process of elaboration and fixation of a conditioned reflex by about 2 times (in control animals the reflex is fixed after 95–127 combinations of the conditional and non-conditional irritation agents, while against the background of administration of the compound according to the present invention —after 49–65 combinations).

Pyracetam in the dose of 500 mg/kg is inactive, while in the dose of 1.000 mg/kg it causes an effect similar to that produced by the compound according to the present inventuion in the dose of 250 mg/kg.

The compound according to the present invention also provides a positive effect on performing an elaborated conditioned reflex of avoidance. In the dose of 250mg/kg the latent period of the conditioned reflex is lowered by more than 2 times as compared to the control (in control rats the latent period is equal to 2.14±0.71s, while in the rats administered with the compound according to the present invention it is equal to 0.87±0.32s).

Pyracetam produces a similar effect(reduces the latent period of the reflex to 0.98±0.29 sec) only when administered in the dose of 1.000 mg/kg.

Therefore, the compound according to the present invention facilitates the process of learning in rats and improves performing of the conditioned response of avoidance, whereas pyracetam in these tests is less active (the effective dose of the compound according to the present invention is 250 kg/mg, that of pyracetam is 1.000 mg/kg).

The study of the effect on processes of consolidation (fixation) of memory was carried out on 400 nondescript male white mice with a mass of 18-20 g using the procedure of a conditioned reflex of passive avoidance in a two-chamber unit, one of the chambers being darkened. In the bottom of the dark chamber an electrode floor is mounted, to which an electric current (50-60 V) can be applied.

Due to their biological specific features, mice prefer to stay in the dark chamber. At the end of the exposure lasting for 180 seconds of the residence of an animal in the dark chamber which, as a rule, actually takes place, an electric current is applied to the irritating device and a mouse is forced to leave its shelter.

Therefore, after a single-time training a conditioned reflex of passive avoidance is elaborated in mice. The resproduction of the effect which is evaluated by the laten period time (in seconds) of the visit to the dark chamber (or by the time of residence in the light chamber) was effected after 24 hours.

The compound according to the present invention and pyracetam were administered in doses of 200-250 mg/kg (pyracetam also in the dose of 1,000 mg/kg) intraperitoneally right after elaboration of the conditioned reflex. It has been found that the compound according to the present invention in the dose of 200 mg/kg extends the duration of the latent period of the reflex to 136.2±6.6 seconds (the value in the control is equal to 102±6.9 s). A similar effect of extension of the latent period of the reflex for pyracetam occurs only in the dose of 1.000 mg/kg.

If the data obtained are represented in per cent (the 100% base is assumable the duration of the latent period of a visit to the dark chamber in the control group), then the latent period of the conditioned reflex of passive avoidance after the administration of the compound according to the present invention in the dose of 200 mg/kg is extended by 33.0%, while after the administration of pyracetam in the dose of 1.000 mg/kg —by 33.7%. In lower doses pyracetam is inactive. The efficiency of the positive influence of the compound according to the present invention upon dose increasing up to 500 mg/kg does not grow.

Therefore, the compound according to the present invention provides a positive effect on processes of consolidation (fixation) of the obtained information and is effective, for this parameter, in the dose of 200 mg/kg, i.e. 5 times lower than pyracetam. The compound according to the present invention extends the latent period of a conditional reflex of passive avoidance by 33% as compared to the control, while pyracetam causes the same effect only in the dose of 1.000 mg/kg.

Consequently, the experiments have shown that the compound according to the present invention provides a positive effect on the learning speed, performing of the elaborated conditional reflex and processes of memory consolidation. The compound according to the present invention is effective in doses by 4-5 time ssmaller than those of pyracetam.

The interaction of the compound according to the present invention with thiosemicarbazide—a specific antagonist of gamma-aminobutyric acid (GABA) was also studied.

Due to the fact that in functioning of the brain, in particular in processes of learning and memorizing, gammaaminobutyric acid (GABA) plays an important role, the possibility of the presence of a GABA-ergic component in the mechanism of action of the compound according to the present invention was studied. To this end, the ability of the compound according to the present invention to prevent convulsions caused by thiosemicarbazide, which is an inhibitor of an enzyme synthesizing gamma-aminobutyric acid, was studied.

The experiments were carried out on 140 white mice of 18-20 g mass. Thiosemicarbazide was administered hypodermally in the dose of 20 mg/kg. The compound according to the present invention was administered intraperitoneally in the doses of 50, 250 and 500 mg/kg 20 minutes after administration of thiosemicarbazide. For every dose 20 mice were used. The presence of the anticonvulsion activity was determined by the change of the latent period of occurrence of convulsions and by extension of the period of death of the animals. The experiments were carried out in comparison with pyracetam. The data thus obtained are given in the following Table 8.

TABLE 8

Effect of the compound according to the present invention and pyracetam on convulsions caused by thiosemicarbazide

| Compound | Dose, mg/kg | Latent period of convulsion occurrence (min) | Time period after which animals die (min) |
| --- | --- | --- | --- |
| Control (0.9 solution tion of NaCl) | — | 63.5 (57.1-69.9) | 69.5 (65.8-73.2) |
| Compound of the present invention | 50 | 59 (51.5-66.5) | 76 (64-88) |
|  | 250 | 82.6 (76.1-89.1) | 100.8 (93.5-108.1) |
|  | 500 | 80 (75.6-86.4) | 105 (95-115) |
| Pyracetam | 1000 | 66.6 (61.0-72.2) | 79.9 (64-96.8) |
|  | 2000 | 70.6 (65.6-75.6) | 82 (73.6-90.4) |

As it is seen from the Table, the compound according to the present invention, as compared to the control, when administered intraperitoneally in the doses of 250 and 500 mg/kg results in extension of the latent period of occurrence of convulsions by 25-30% and extends the period of death occurrence by 45-50%.

Pyracetam administered in a dose 4 times that of the compound according to the present invention, also in comparison with the control, extends the latent period of occurrence of convulsions only by 10%, and the death —by 17%.

The thus-obtained data point to the possibility of participation of GABA-ergic structures of the brain in the mechanism of action of the compound according to the present invention.

The pyracetam a similar effect is pronounced but very slightly and in higher doses.

The study of toxicity and a general effect of the compound according to the present invention was effected on mice with a mass of 18–20 g upon an intraperitoneal administration of the compound according to the present invention in doses of from 100 to 1.500 mg/kg.

It has been found that suppression of a general state of the animals starts with the dose of 250 mg/kg. For the compound according to the present invention the LD$_{50}$ is equal to 1.200 mg/kg.

It should be noted that low-toxic compounds are classified as compounds having their LD$_{50}$ exceeding 1.00 mg/kg, wherefore the compound according to the present invention may be considered as low-toxic.

A process for preparing the compound of the invention is also a subject of this invention.

According to the invention, a process for preparing the novel compound, 1-thiocarbamylmethylpyrrolidine-2-thione, resides in that derivatives of pyrrolidone-2 of the general formula

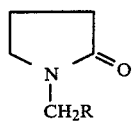

wherein R is nitrile of carbamyl, are reacted with phosporus pentasulphide in an inert non-polar solvent at a temperature above room temperature, followed by treating the resulting precipitate with water under boiling, and isolation of the desired product.

As the inert non-polar solvent it is preferable to use xylene or benzene.

With a view to increasing the yield of the desired product, it is advisable to carry out the process at a temperature of 80° to 145° C.

The process is conducted in accordance with the following scheme:

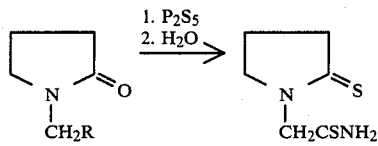

wherein R is CH—, CONH$_2$—.

The pyrrolidone-2 derivative of said general formula is treated with phosphorus pentasulphide in an inert non-polar solvent at a temperature higher than room temperature, preferably at 8°–145° C.

As the inert non-polar solvent use can be made of any suitable solvent, e.g., mesitylene, toluene, preferably xylene, benzene. The precipitate formed in the course of the reaction is treated with water under boiling. The resulting reaction mass is filtered, the mother liquor is cooled, the precipitated desired product is isolated.

The yield of the desired product is up to 65 wt. %, m.p. 156°–158° C. (from isopropanol).

For a better understanding of the present invention, some specific examples illustrating the process for preparing 1-thiocarbamylmethylpyrrolidine-2-thione are given hereinbelow.

EXAMPLE 1

A suspension consisting of 21.6 g (0.175 mole) of 1-cyanomethyl-2-oxopyrrolidone, 37.9 g (0.175 mole) of phosphorus pentasulphide, and 850 of dry xylene is heated at the temperature of 130° C. for 4 hours. The mixture is cooled to room temperature, the precipitate is filtered off and heated at reflux in 2500 ml of water for 30 minutes.

The reaction mass is filtered. The mother liquor is cooled at a temperature of 8°–10° C. The precipitated product is filtered off to give 14.8 g of 1-thiocarbamyl-methylpyrrolidine-2-thione, m.p. 154°–156° C.

The mother liquor is evaporated to give additional 4.8 g of the desired product, m.p. 153°–155° C.

The total yield of 1-thiocarbamylmethylpyrrolidine-2-thione is 19.6 g (64.5 wt. %).

For analysis the desired product is crystallized from isopropanol, m.p. 156°–158° C.

Found, %: C 41.46, H 5.74, N 16.33, S 36.81, C$_6$H$_{10}$N$_2$S$_2$. Calculated, %: C 41.35, H 5.78. N 16.07, S 36.80. IR-spectrum), cm$^{-1}$: 1.630; 3,110; 3.260 cm$^{-1}$ (NH$_2$); 1.120 cm$^{-1}$ (C=S).

EXAMPLE 2

Under the conditions similar to those described in Example 1 hereinabove, but using toluene as the solvent and carrying out the process at the temperature of 110° C. the desired product is obtained in the yield of 49% by weight; melting point is 154°–156° C.

EXAMPLE 3

Under the conditions similar to those of Example 1, but using mesitylene as the solvent and carrying out the process at a temperature of 140°–145° C., the desired product is obtained in the yield of 41% by weight; melting point is 154°–156° C.

EXAMPLE 4

Under the conditions similar to those described in Example 1 hereinbefore, but using benzene as the solvent and carrying out the process at the temperature of 80° C. the desired product is obtained in the yield of 62% by weight; the melting point is 154°–156° C.

EXAMPLE 5

A suspension consisting of 2.8 g (0.02 mole) of 1carbomylmethylpyrrolidone-2 and 8.8 g (0.04 mole) of phosphorus pentasulphide and 50 ml of dry xylene is heated for 4 hours at the temperature of 130° C.

The mixture is cooled, the precipitate is filteredoff and refluxed for 30 minutes in 150 ml of water. The reaction mass is filtered, the mother liquor is cooled at 8°–10° C. The precipitated product is filtered-off to give 1.1 g (32% by weight) of 1-thiocarbamylmethylpyrrolidine-2-thione melting at 154°–156° C.

INDUSTRIAL APPLICABILITY

The compound of the invention exhibits antihypoxic and nootropic activity and can be useful in medicine for the prophylaxis and therapy of states accompanied or caused by hypoxia: ischemia of organs and tissues (brain and heat ischemia), recovery after ischemic injuries and states; surgery and therapy of infarctions and strokes; anti-ischemic conservation of organs and tissues with a view to their transplantation; gerontology, neurological deficiency; prophylaxis and therapy of hypoxia in healthy people when climbing mountains, in intoxications with prohypoxants (metahaemoglobin-forming and respiratory chain-blocking agents).

We claim:

1. 1-Thiocarbamylmethylpyrrolidine-2-thione of the following formula:

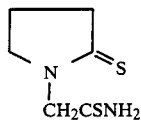

2. A pharmaceutical composition useful for imparting antihypoxic and nootropic activity, said composition comprised of 1-thiocarbamylmethylpyrrolidine-2-thione of the formula

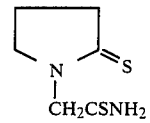

and a pharmaceutically acceptable carrier.

3. A method for imparting an antihypoxic effect to a subject which comprises administering to said subject an antihypoxic-effective amount of the pharmaceutical composition of claim 2.

4. A method for imparting nootropic activity to a subject which comprises administering to said subject a nootropic-effective amount of the pharmaceutical composition of claim 2.

* * * * *